(12) United States Patent
Pengo

(10) Patent No.: US 11,147,598 B2
(45) Date of Patent: Oct. 19, 2021

(54) BONE FIXATION APPARATUS

(71) Applicant: Bioscience Medical Group Ltd, Neuchatel (CH)

(72) Inventor: José Roberto Pengo, Jau (BR)

(73) Assignee: Bioscience Medical Group Ltd., Neuchâtel (CH)

(*) Notice: Subject to any disclaimer, the term of this patent is extended or adjusted under 35 U.S.C. 154(b) by 23 days.

(21) Appl. No.: 15/567,922

(22) PCT Filed: Apr. 20, 2015

(86) PCT No.: PCT/EP2015/058492
§ 371 (c)(1),
(2) Date: Oct. 19, 2017

(87) PCT Pub. No.: WO2016/169578
PCT Pub. Date: Oct. 27, 2016

(65) Prior Publication Data
US 2018/0110550 A1    Apr. 26, 2018

(51) Int. Cl.
*A61B 17/80*     (2006.01)
*A61N 1/05*      (2006.01)
*A61N 1/32*      (2006.01)
*A61N 2/00*      (2006.01)
*G01B 7/16*      (2006.01)
*A61N 7/00*      (2006.01)
*A61N 2/02*      (2006.01)
*A61N 2/06*      (2006.01)

(52) U.S. Cl.
CPC ............ *A61B 17/8023* (2013.01); *A61N 1/05* (2013.01); *A61N 1/326* (2013.01); *A61N 2/002* (2013.01); *A61N 2/004* (2013.01); *A61N 7/00* (2013.01); *G01B 7/16* (2013.01); *A61B 17/8014* (2013.01); *A61N 2/02* (2013.01); *A61N 2/06* (2013.01); *A61N 2007/0013* (2013.01)

(58) Field of Classification Search
CPC ...... A61B 17/80; A61B 17/8023; A61N 1/05; A61N 1/326; A61N 2/002; A61N 2/004
See application file for complete search history.

(56) References Cited

U.S. PATENT DOCUMENTS 2,501,978 A * 3/1950 Wichman ............... A61B 17/80
                                                       606/71
5,292,252 A    3/1994 Nickerson et al.
(Continued)

FOREIGN PATENT DOCUMENTS

BR    PI-0606073 A    5/2008
CN    204092157 U     1/2015
EP    2759271 A1      7/2014

OTHER PUBLICATIONS

International Search Report and Written Opinion of PCT/EP2015/058492, dated Jan. 14, 2016, 14 pages.

*Primary Examiner* — Christopher J Beccia
(74) *Attorney, Agent, or Firm* — Blank Rome LLP

(57) ABSTRACT

Implantable bone fixations apparatus comprising a pair of plates (1 and 1') provided with holes (11, 12, 13) for receiving compression and/or locking screws and with longitudinal slots (15), characterized by a union element (3) disposed between the plates (1, 1') such as to bridge the bone parts that need to be united, the union element (3) comprising rods that cooperate with the longitudinal slots (15) of the plates (1, 1').

14 Claims, 15 Drawing Sheets

(56) References Cited

U.S. PATENT DOCUMENTS

| | | | |
|---|---|---|---|
| 8,380,319 B2 | 2/2013 | Berger | |
| 8,425,395 B2* | 4/2013 | Kraus | A61N 2/02 |
| | | | 600/13 |
| 2004/0116931 A1* | 6/2004 | Carlson | A61B 17/7011 |
| | | | 606/70 |
| 2006/0276794 A1* | 12/2006 | Stern | A61B 17/8023 |
| | | | 606/71 |
| 2007/0265682 A1* | 11/2007 | Wiegmann | A61C 8/0007 |
| | | | 607/51 |
| 2008/0255556 A1* | 10/2008 | Berger | A61B 17/8605 |
| | | | 606/60 |
| 2010/0036467 A1* | 2/2010 | Kraus | A61N 1/05 |
| | | | 607/116 |
| 2011/0098603 A1 | 4/2011 | Deirmengian et al. | |
| 2013/0190654 A1* | 7/2013 | Deirmengian | A61B 5/103 |
| | | | 600/587 |
| 2015/0080636 A1* | 3/2015 | Rogachefsky | A61B 17/86 |
| | | | 600/13 |
| 2015/0094522 A1* | 4/2015 | Mauger | H04R 25/606 |
| | | | 600/25 |
| 2015/0289911 A1* | 10/2015 | Beyar | A61B 17/7059 |
| | | | 606/70 |
| 2015/0306373 A1* | 10/2015 | Bouton | A61N 1/0484 |
| | | | 607/48 |

* cited by examiner

BONE FIXATION APPARATUS

RELATED APPLICATION

This application is a national phase of PCT/EP2015/058492, filed on Apr. 20, 2015. The entire content of that application is hereby incorporated by reference.

FIELD OF THE INVENTION

The present invention relates, in embodiments, to a bone fixation apparatus, in particular to an orthopaedic plate that can be usefully employed for securing together adjacent bones or bone segments. Importantly, the fixation apparatuses of present invention may include by design a certain degree of compliance that consent limited, but clinically significant relative movement between the adjacent parts, and/or embedded stimulation devices, in particular of electronic nature. The fixation devices of the present invention can be used for reducing and healing fractured bones. This is not however their sole application or indication.

DESCRIPTION OF RELATED ART

Several variant of internal bone fixators are known in the art. Such devices are mostly constructed by solid metallic plates, variously fashioned as to adapt to the anatomy of a specific bone or section thereof, and are fastened to the bone by means of suitable means, for example cortical screws inserted in the bone and whose heads engage in suitable openings of the plates. Conventional fixation plates exhibit in the rule zero or very little flexibility, and leave little or no room for adjustments during surgery according to the observed needs by the clinician.

These devices have been used with good success in the therapy of fractures, yet they are not without shortcomings, In particular, they may be ill-tolerated by the human body, in particular in presence of bone fractures. Moreover, conventional implants are liable to affect the exact point of fracture by direct contact, which may cause loss of power and irrigation supply of bone tissue, resulting in the death of bone cells and delaying the consolidation of the fractured bone.

Patent application BRPI0606073 describes a fixation system of a bone plate to a bone by means of screws.

There is also substantial literature describing an improvement in bone healing with the stimulation of an electric or magnetic field across a bone fracture. Such methods are of particular interest especially for delayed or non-union of fractures. In most of the studies time-varying electro-magnetic fields or pulsed electromagnetic fields (PEMF) are used. While most studies have been conducted with external generators, it is also known to include an electromagnetic stimulation unit in an implantable bone plate, for example as disclosed by patent application US2007265682, or in orthopaedic screws, as taught by U.S. Pat. Nos. 8,380,319, 5,292,252, and US2010036467.

A common limitation of these stimulation methods is that they do not allow a precise control of the field parameters (amplitude, frequency, shape of signal) at the fracture site, particularly when external generators are used. When, one other side, the field generator is embedded, it may be difficult to attain a sufficient intensity of field at the fracture site.

The implant of a fixation device on a live bone involves considerable mechanical stress both the implant and to the bone on which it is fastened. These stresses are both generated during the surgical operation and the subsequent healing process. It is known that a moderate amount of mechanical stress at the fracture site promotes the formation of bone tissue, and is beneficial to the healing process. On the other hand it is conceivable that excessive or misdirected stresses might have the opposite effect. Conventional bone fixation devices do not offer the possibility of measuring and monitoring mechanical stresses.

An aim of the present invention is therefore the provision of a bone fixation and reduction system that allows a better positioning of the plate to the bone and consents a limited measure of movement to the fractured bone parts. Another aim of the present invention is the provision of an adjustable bone fixation apparatus.

A further aim of the present invention is the provision of a bone fixation system that can be equipped by embedded electronic units that allows the measure and the monitoring of mechanical stresses, and/or a stimulation of the fracture site, be it by electric, magnetic, photonic or radiation fields by acoustic or vibrational waves, or by other suitable electromechanical stimulations means.

Another aim of the present invention is to design a device enabling an accurate control of the electrical or magnetic field value at the fracture side.

BRIEF SUMMARY OF THE INVENTION

According to the invention, these aims are achieved by means of the object of the appended claims, and in particular, by a bone fixation apparatus that comprises plates provided with holes for receiving fixation, compression or locking screws. In preferred embodiments the plates are provided with longitudinal slots, for example of quadrangular section, that cooperate with a union element that may be "U" shaped, and preferably is disposed such as to bridge two bone parts that need to be united.

In further embodiments, the plates, or the union element, or the screw that fasten the fixation system to the bone, are equipped with microelectronic and/or microfluidic elements, whose function is to promote bone healing by generating an electric or magnetic field, or a vibration or a sonic wave, or else to monitor strain or forces at or close to the fracture site.

BRIEF DESCRIPTION OF THE DRAWINGS

The invention will be better understood with the aid of the description of an embodiment given by way of example and illustrated by the figures, in which.

DETAILED DESCRIPTION OF POSSIBLE EMBODIMENTS OF THE INVENTION

Figure 1:
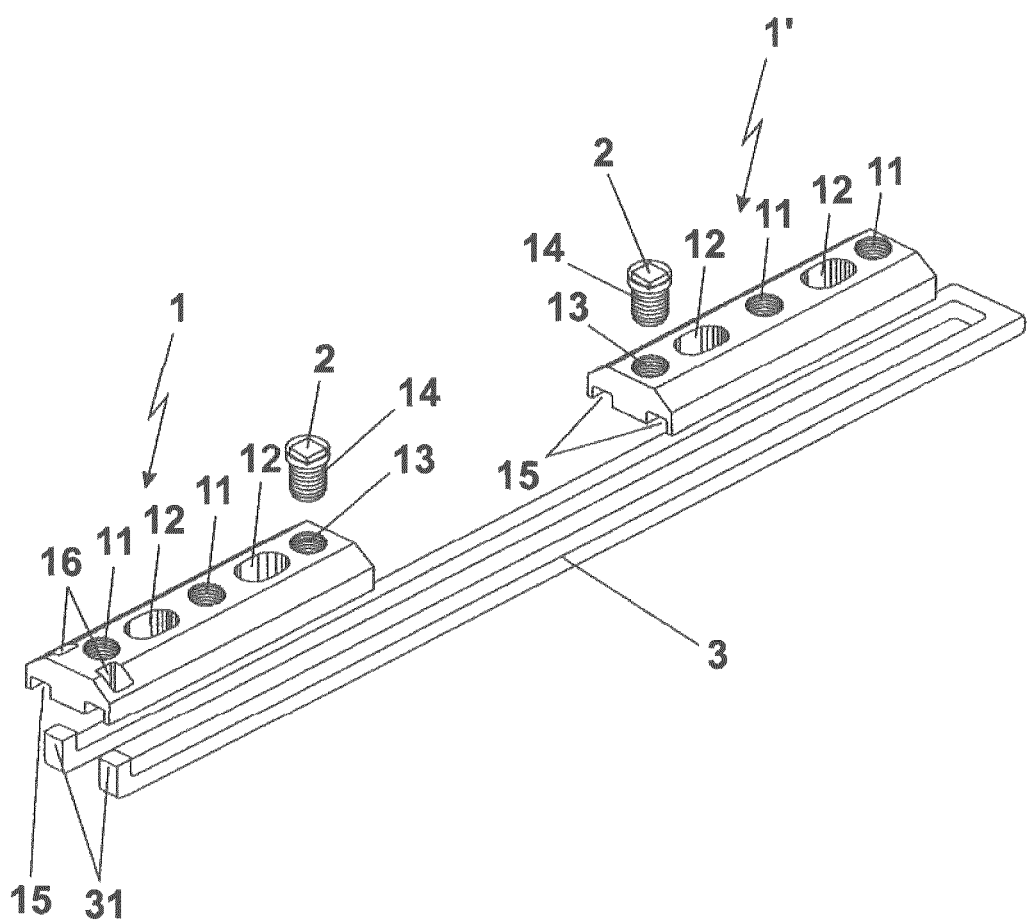
FIG. 1 shows an exploded view of a possible realization of the bone fixation device of the invention.
Figure 2:
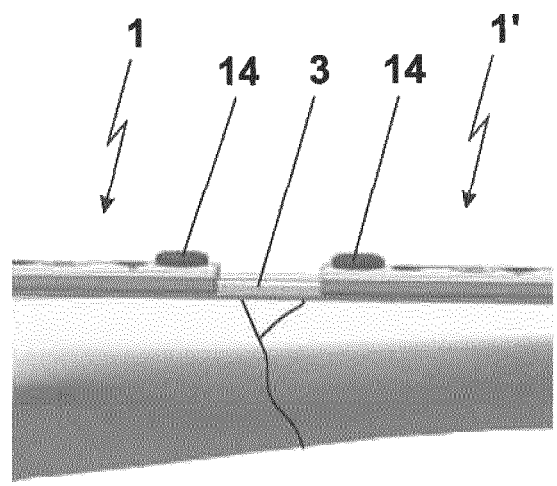
FIG. 2 illustrates schematically a possible implantation situation of the device of the invention.

A possible structure of the inventive fixation device will now be described with reference to FIGS. 1 and 2. The device can be made of different materials, such as stainless steel, titanium alloys, cobalt alloys, chromium, molybdenum or other suitable metal alloys, polymers or composite materials such as carbon fibre. It comprise comprises a pair of plates 1 and 1', whose lengths and widths are determined according to the bone to which the fixation device is implanted. Plates 1 and 1' are represented in the drawing with the same overall dimensions, which may be a desirable simplification, but is not an essential feature of the invention.

Plates 1, 1' are provided on the top face with threaded holes 11, 13 in which locking screws 2 can be inserted, and moreover present oblong holes 12, which may optionally be threaded and are foreseen for using compression screws, when necessary.

The plates 1, 1' are provided in their lower side (the site that is close to the bone, when the implant is in its normal intended position) with slots 15 that interact with the union element 3 that is placed between the plates and the bone. The union element 3 presents in this variant a pair of parallel rods united at one end, which results in an "U" shape, and the section of the rods corresponds to those of the slots in the plates 1, 1' such as to allow relative motion and accurate positioning between the rods 3 and the plates 1, 1'. Length, transversal dimensions and shapes of the rods 3 and of the slots 15 are chosen in relation with the anatomy of the implant site and the foreseeable mechanical solicitations. The rods of the union element 3 are united at one extremity by a short traverse element (the bottom of the "U") an present at another extremity a pair of protrusions 31 that interact with corresponding openings 16 in the plate 1.

In a non-represented variant of the invention the two parallel rods 3 could be replaced by a single rod, placed centrally or laterally.

According to an important variant of the invention, the inner pair of threaded holes 13, that is to say the pair of threaded holes that is closer to the fracture site, is occupied in both plate by fixation screws equipped with embedded electronic or magnetic devices 2, whose function will be further detailed in the following. In other variants of the invention, electronic or magnetic devices may be placed, on the plates 1, 1' and/or on the union element 3, preferably in proximity with the fracture region.

These devices 2, may include permanent magnets or electromagnets, preferably of opposite polarities, which give rise to a magnetic field between 0.1 and 3000 or 4000 gauss. The appropriate field intensity and treatment conditions will be determined based on clinical indications.

According to another embodiment, the electronic or magnetic devices 2 are arranged to generate a time-variable electric or magnetic field, or a vibration.

Figure 10:
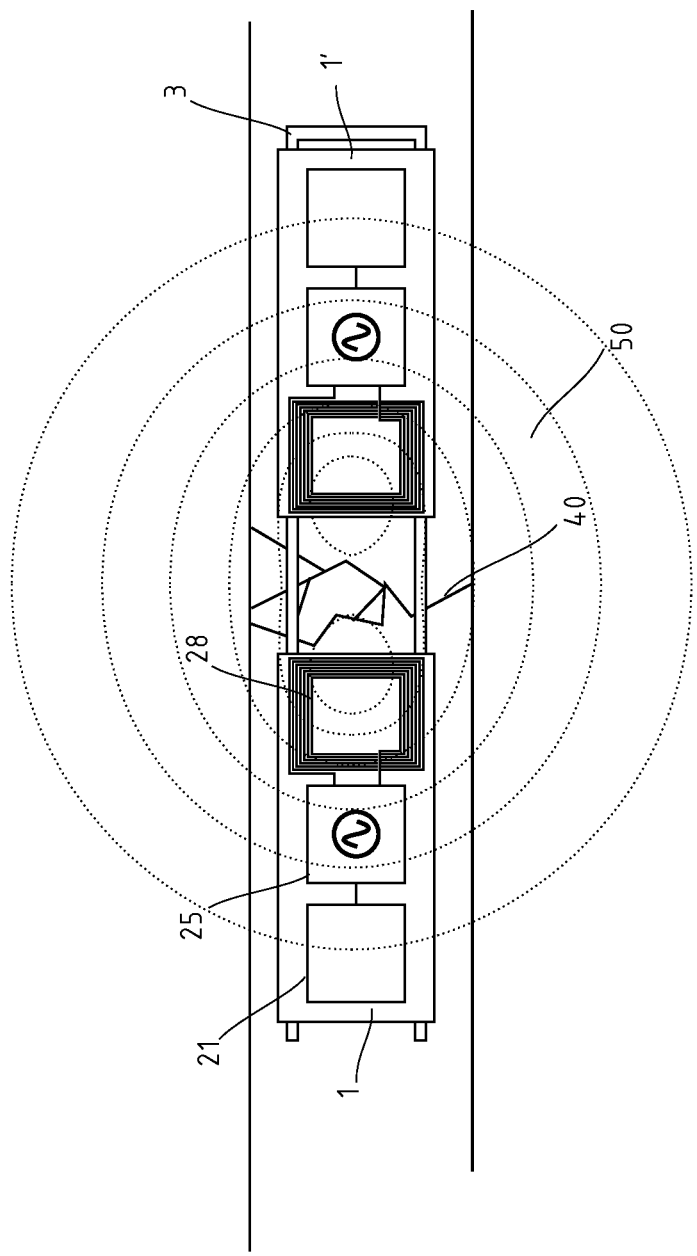
FIG. 10 illustrates schematically a possible structure of an embodiment of the invention including active electronic stimulator devices.

In a possible variant, that is represented schematically on FIG. 10 the electronic or magnetic devices 2 include an energy source 21, for example an electrochemical battery, and a field generator, such as an electronic oscillator 25 coupled to a suitable antenna or coil 28, in order to create a time-variable electric or magnetic field 50 at the fracture site 50 having predetermined values of amplitude, frequency, and/or shape.

In some applications, however, particularly where the dimension of the fixation device are limited, the place for an electrochemical battery may not be available. In this case, according to another variant, the energy source 21 may be an inductive receiver coupled with a suitable external generator. In this variant, the electromagnetic energy provided from the outside and converted to an electric or magnetic field with appropriate constant or time-varying signal in order to accelerate bone healing. Preferably, the energy source 21 may include a rechargeable cell that allows operation over extended periods, and can be recharged by means of the external generator.

In non-represented variants of the present invention, the coils 28 could be replaced by electrodes, in order to generate an electric field or an electric current, either static or time-variable, or by vibration transducers, for example piezoelectric or magnetostrictive transducers that give rise to vibration at sonic or ultrasonic frequency in the fracture zone.

Figure 11:
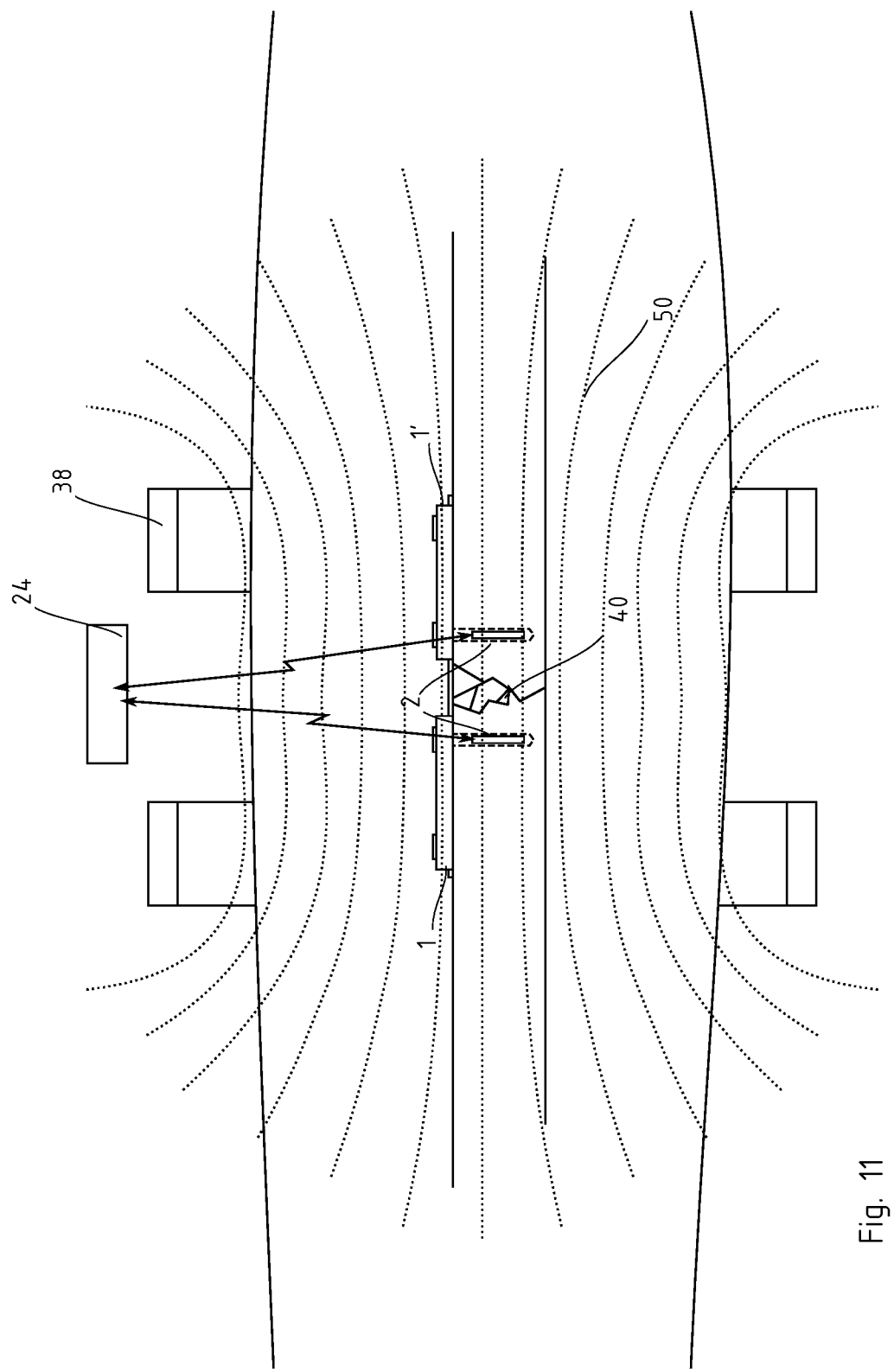
FIG. 11 illustrates another embodiment of the present invention, which has electronic stimulation and/or diagnostic devices that communicate wirelessly with an external unit

A further embodiment of the invention will now be presented with reference to the FIG. 11. In this realization, the fracture, immobilized by a fixation device having the mechanical structure described above and comprises one or more electronic or magnetic devices 2, for example in the innermost screws 2, or else on the plates 1, 1' These device could fulfil several functions:

a. In a first variant, the fractured limb is treated with a magnetic field 50 generated by an eternal device 38 (here represented schematically by a pair of coils but which could, however have any other suitable structure) the devices 2 may include an high-permeability magnetic material that distorts the magnetic field 50 and concentrates it in the fracture zone 40, thereby enhancing its therapeutic effect.

b. According to another variant, the devices 2 include a magneto-acoustic transducer, for example a magnetostrictive material that, when invested by a variable magnetic field 50 generated by external device 38, produces a vibration with the same frequency. In this way the magnetic stimulator devices 2 produce a vibration directly in the fracture zone, or immediately adjacent thereto.

c. In a further variant of the invention, the embedded devices 2 are electronic transducers that communicate wirelessly with, and preferably receive an energy supply from, an external RFID interface 24. The transducers 2 transmit a local value of the electric or magnetic field 50 at the fracture region 40, thus providing a feedback loop that allows controlling precisely the field at the bone level.

d. According to another variant, the embedded devices 2 include strain, force, or displacement transducers that communicate the mechanical stress at the fracture site to the RFID interface 24. This information can be used by the surgeon when the fixation device is implanted, and later on to monitor the healing process. In this case, the external field generator 38 may be omitted. The transducers embedded in devices 2 may comprise strain gauge, or MEMS sensors, for example.

e. In yet another variant, the embedded devices 2 are position tags that can be located precisely by the external RFID interface 24. In this manner, they provide a useful positioning aid to the surgeon during the implant, and can be used to monitor the bone healing process afterwards.

Figure 12:
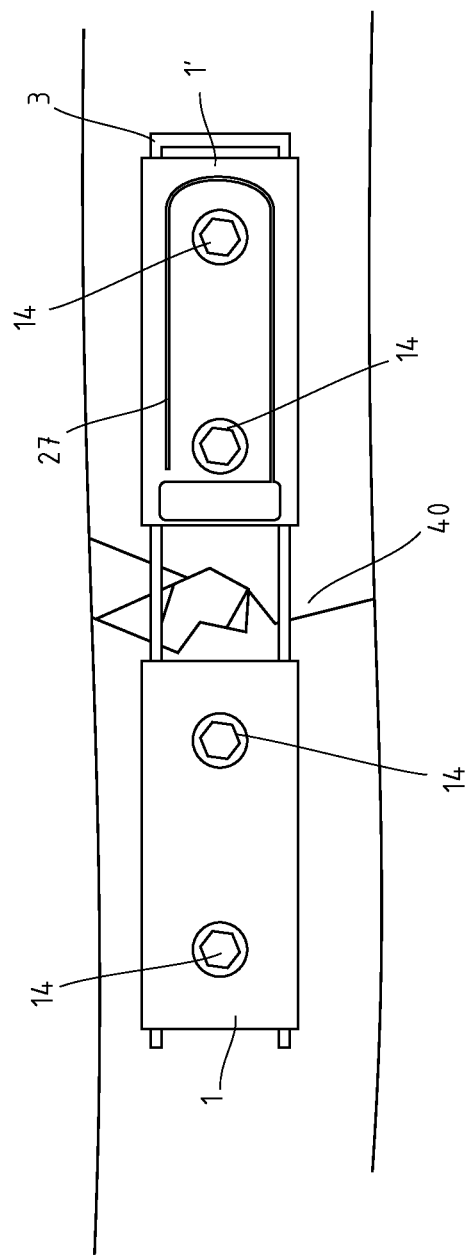
FIG. 12 illustrates schematically an embodiment of the present invention comprising a microfluidic device
Figure 13A:
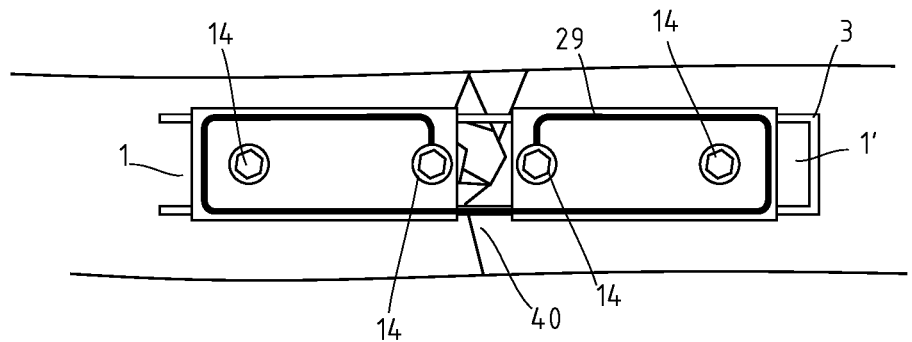
FIGS. 13a and 13b illustrate schematically another embodiment of the present invention comprising a microfluidic device.
Figure 13B:
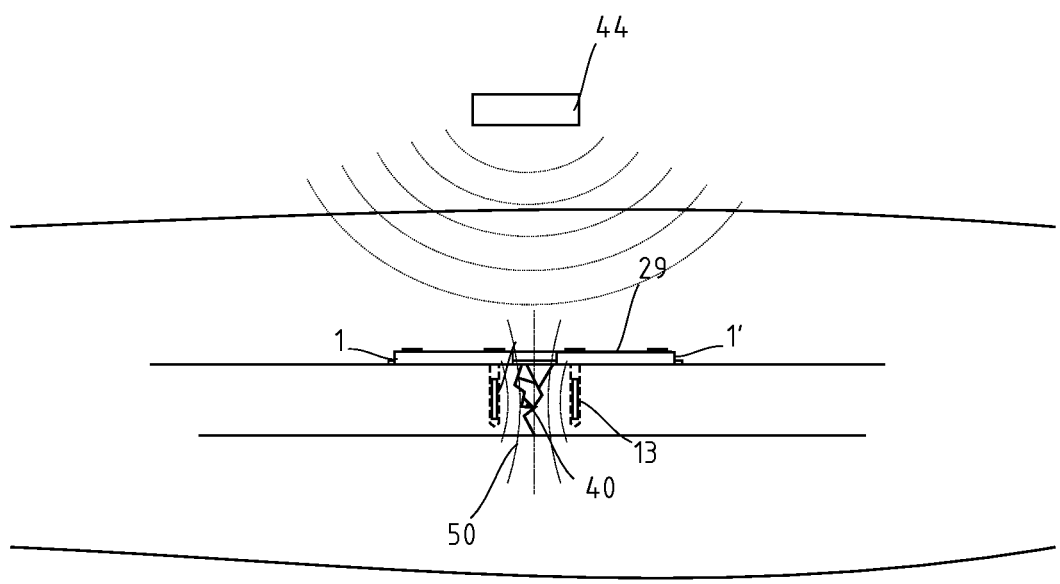

FIG. 12 illustrates a further variant of the fixation device of the invention comprising a microfluidic strain sensor 27. The strain sensor 27 includes a deformable reservoir filled with an incompressible fluid, and a microchannel in which a fluid-gas interface is present. The position of the interface is a measure of the volumic deformation of the reservoir and can be read by suitable medical imaging means, for example ultrasonically or by radioscopy.

Figure 3:
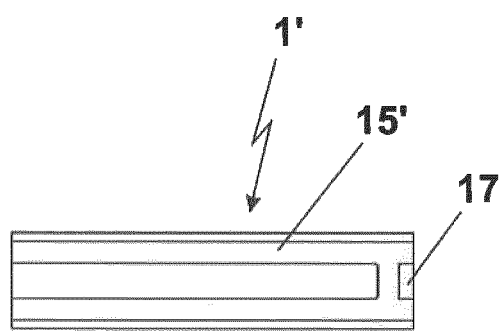
FIG. 3 show a bottom view of an embodiment of the present invention in which one plate presents a "H" channel forming a blocking wall.

Reverting to FIG. 3, in an embodiment of the present invention the plate 1' (here seen from below) is provided with a slots 15' having rectangular cross section and arranged in an "H" configuration. This leaves at one end of the plate 1' a wall or indentation 17 that, interacting with the "U" shaped rods 3, hinders the movements of the plate 1' in both directions.

Figure 4:
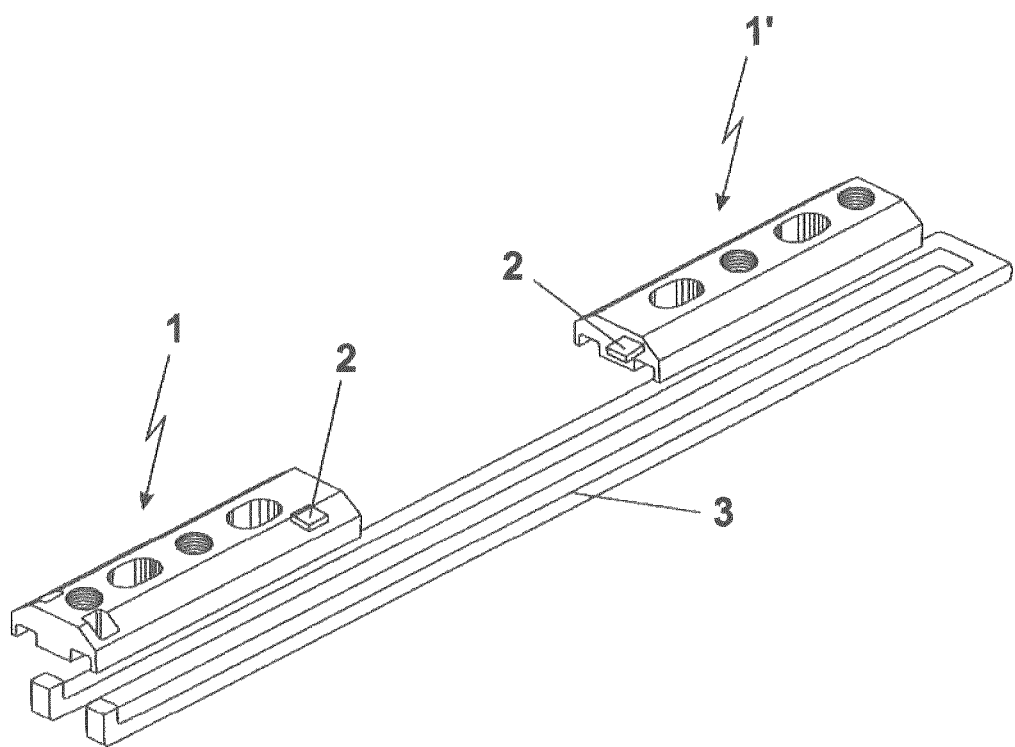
FIG. 4 illustrates schematically an embodiment of the present invention that includes embedded microelectronic circuits.
Figure 5:
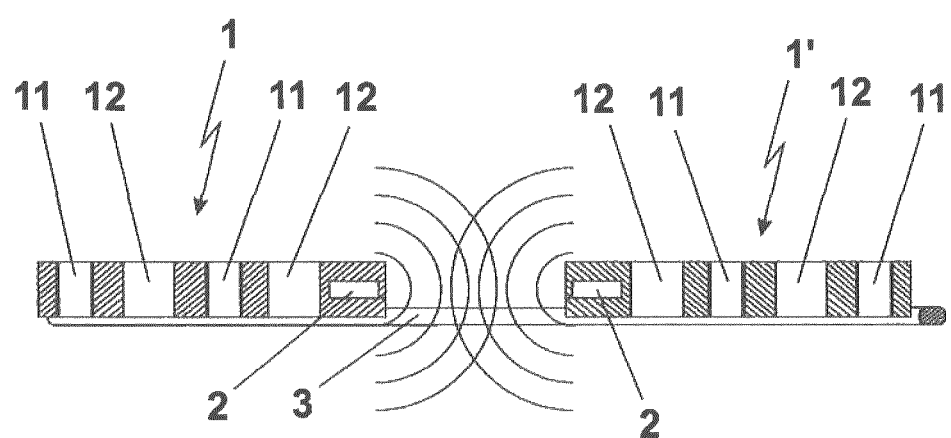
FIG. 5 illustrates, in side view, the stimulating action of the embedded microelectronic circuits in a variant of the invention.
Figure 6:
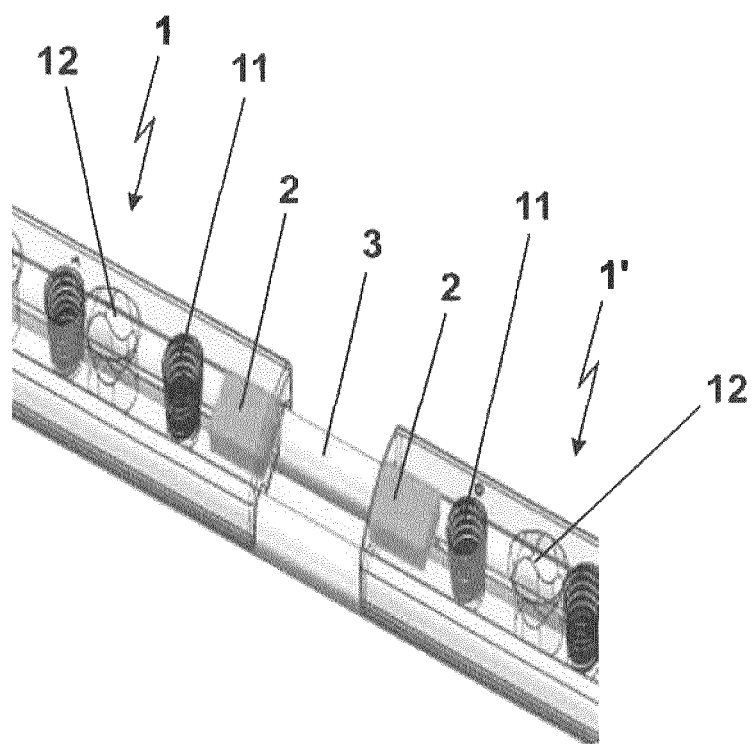
FIG. 6 illustrates a variant of the invention with embedded microelectronic devices.

FIGS. 4 to 6 relate to another embodiment in with embedded electronic or magnetic devices 2 are affixed to the plates 1, 1', for example to their internal edges. As in the previous case, the electronic devices 2 may include sources of electric or magnetic field, which may be generated autonomously or induced by external electric or magnetic fields.

Figure 7:
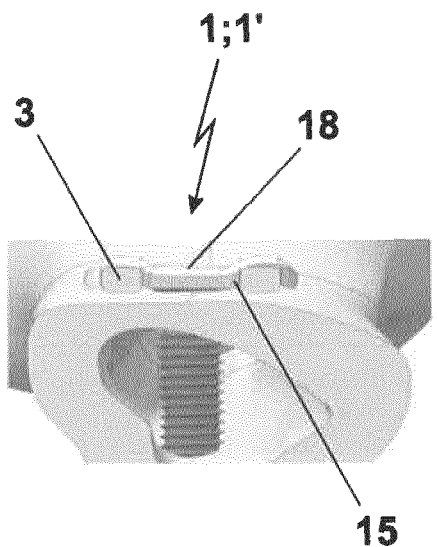
FIG. 7 illustrates, in section, a possible embodiment of the embodiment with lower guide channels and upper central notch.

According to FIG. 7, in an embodiment, the plates 1 and 1' may optionally be provided on the lower face with slots 15 interacting with the rods 3 as detailed above, and present central recess 18 on the upper side.

Figure 8:
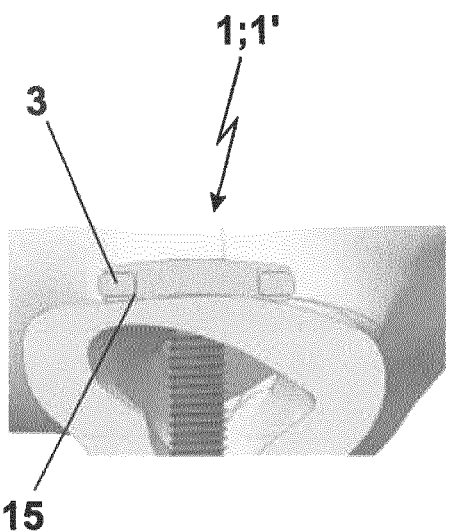
FIG. 8 shows, in section, a detail view of a further embodiment with side guides channel and curved central body.
Figure 9:
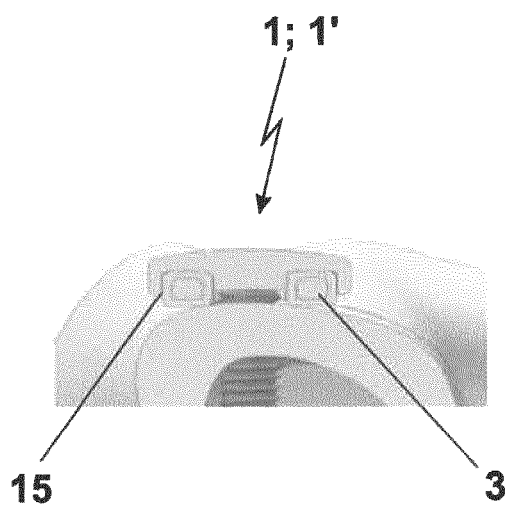
FIG. 9 is a section of an embodiment of the invention with quadrangular tubular rods.

According to FIG. 8, in an embodiment, the plates 1 and 1' may optionally have the slots 15 a central body with curved surfaces. In a further embodiment shown in FIG. 9, the quadrangular rods 3 are tubular.

With the new constructive disposition insert in a multiple bone fixations apparatus, the rod 3 can be previously fixed on the plates or attached during surgery, with dimensions that vary according to the fractured bone to receive the apparatus, where it is fixed by tapping or compression screws holding the plates (1 and 1') on each side of the fracture. This structure allows a certain degree of "movement" at the fracture site that stimulates bone healing, and facilitates the assembly of the implant during the surgery. Importantly, the spacing between the plates can be so chosen that the exact point of fracture between the two plates 1, 1', will be immobilized by the set, but free from direct contact with the implant components. The plates 1, 1' can be positioned precisely on the rods 3, providing greater accuracy in the introduction of the screws in the fractured bone.

The embedded microelectronic devices 2 act directly on the cells of the body, rejuvenating the cells, normalizing the metabolism and circulatory disorders, improving oxygen supplementation in the affected tissues, detoxifying the body and increasing the resistance and self-healing processes of the body. Preferably, these devices do not emit heat or radiations beyond what is strictly necessary and are free from undesirable effects. Since the microelectronic devices are positioned adjacent to the fracture site, the electric, magnetic or vibration stimulation penetrates the target tissue without weakening, which enhances the therapeutic effect. The interaction between the stimulators and the healing bone is preferably indirect, without direct contact.

The modular construction of the implant, in particular in those variants, in which the stimulators are lodged in the screws or in the plates, allows using many different of therapeutic and/or diagnostic devices, with minimal adaptations.

Monitoring of relevant clinical parameters, including strain, forces, temperature, as well as identification and registration information is also possible. These data can be transmitted outside the body by a suitable wireless or RFID link, or may be read by medical imaging.

The modular construction with two plates connected by parallel rods gives to the object of the present invention significant advantages over conventional fixation devices. In particular, the fixation device of the invention is capable of adaptation to different individual anatomic conformations, by sliding the plates along the connection rods. Moreover, by combining plates having different length, thickness, or shape with rods of different lengths, the present invention allows the realization of osteosynthesis implants in a large number of combination, starting from a limited stock of parts.

Figure 14A:
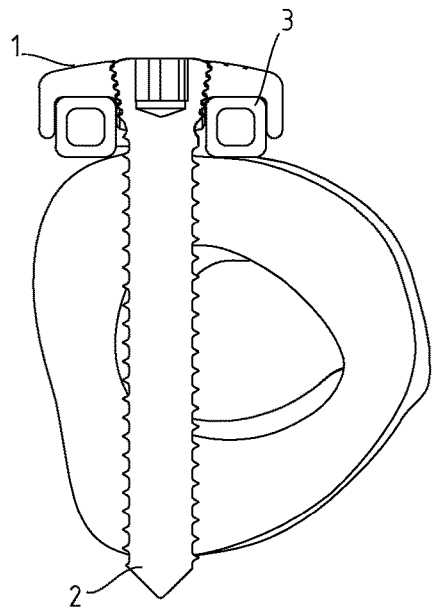
FIGS. 14a and 14b illustrate schematically and in section two variants of the invention in which the parallel rods have square, respectively round section. The device of the invention is shown implaanted in a fracture bone, a tibia in the example.
Figure 14B:
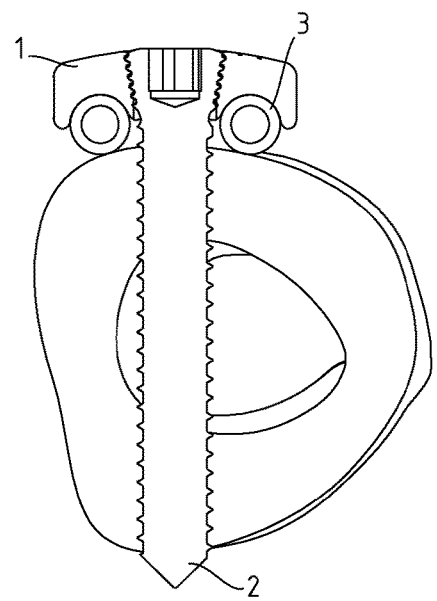
Figure 14C:
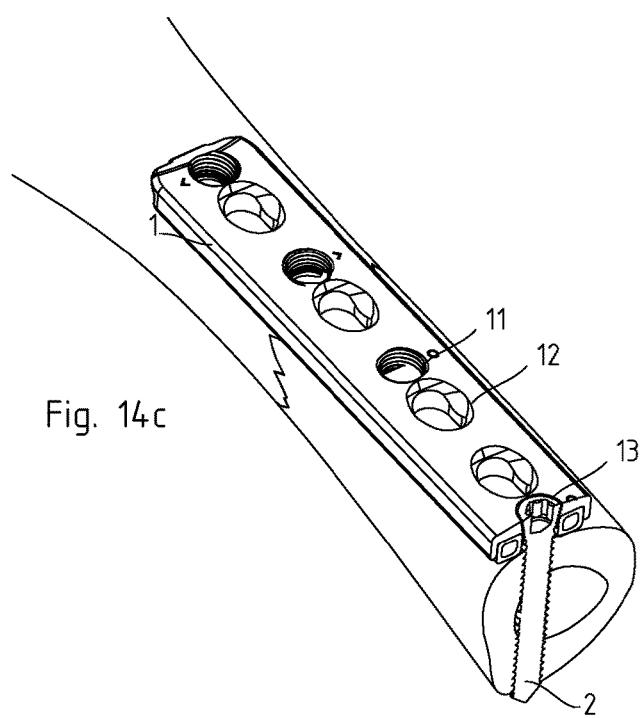
FIG. 14c shows in perspective and in section, the square-rod variant.

With reference to FIGS. 14a-c, it is important to underline that the present invention is not limited to a specific cross-section of the guiding rods 3. These figures show that the plates 1, 1' can be shaped to cooperate with rods 3 of square or round cross-section, or indeed of any possible cross-section. FIG. 14c shows an implant partially fixed to a long bone, in this example a tibia, near to a fracture site.

Figure 15:
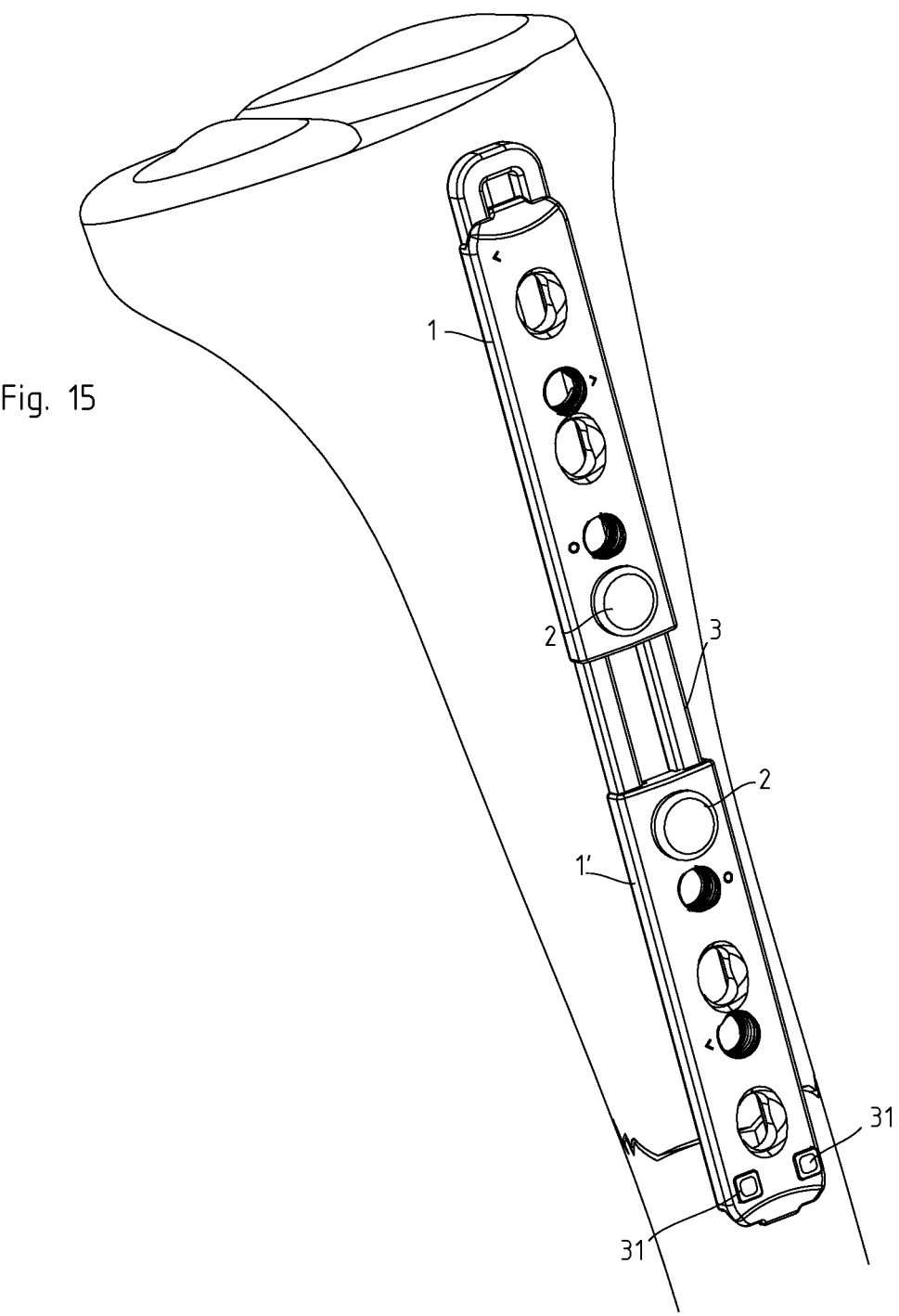
FIG. 15 illustrates with more detail a possible placement of the device of the invention on a human tibia. The device includes two magnetic stimulation devices 2 on the screws.

FIG. 15 illustrates more in detail a possible placement of an ostheosyntesis device according to the present invention on a fractured bone, in this example a tibia. This embodiment of the invention includes a pair of square-section connection rods 3 that are joined together at the proximal end so to form a "U" shape, while in their distal end they present hooks 31 that engage within corresponding apertures in the plate 1' to limit plate sliding. The plates 1 and 1' have each two longitudinal slots in their lower side (meaning by 'lower', the side that is meant to lie on the bone), into which run the rods 3. The plates 1, 1' include a plurality of holes in which fixation screws 2 can be inserted. In the present example, each of the fixation screws 2 include a magnetic device, as mentioned above.

Figure 16:
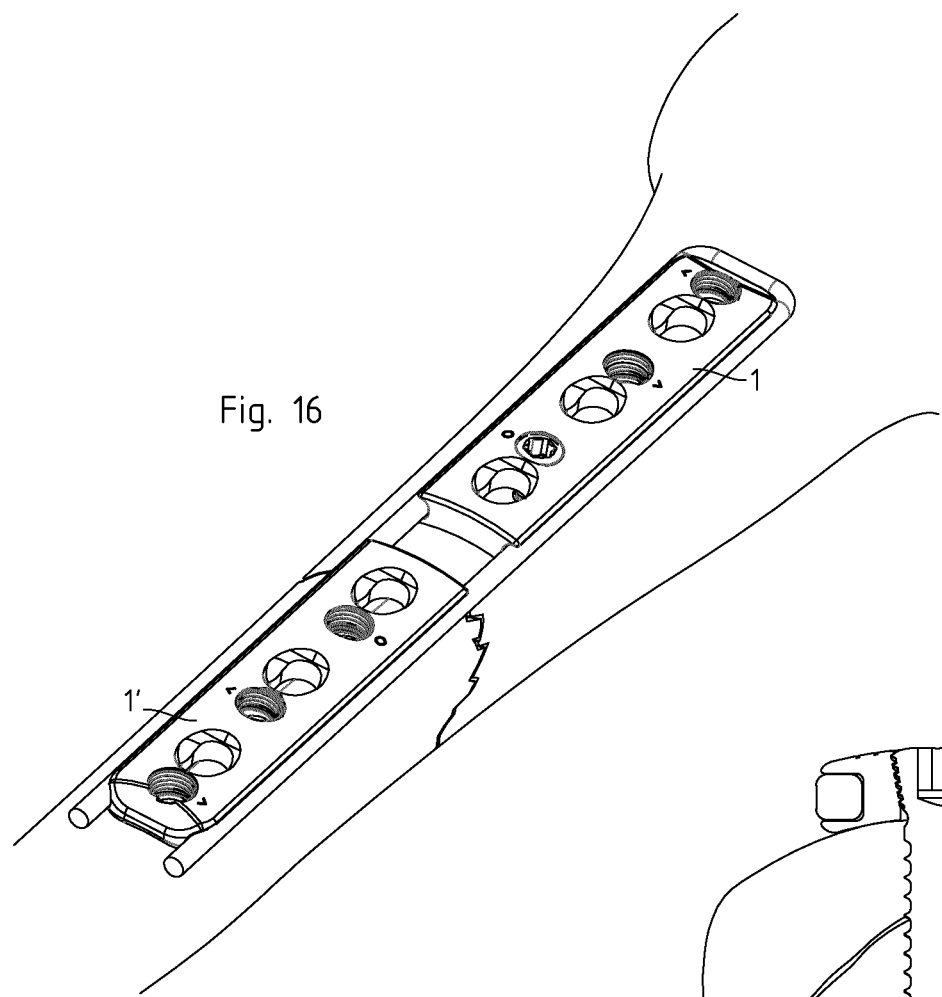
FIG. 16 shows another embodiment of the invention in which the parallel rods are partially embedded in side channels of the plates, such that the rods do not touch the bone, contrary to the previous embodiments.
Figure 17A:
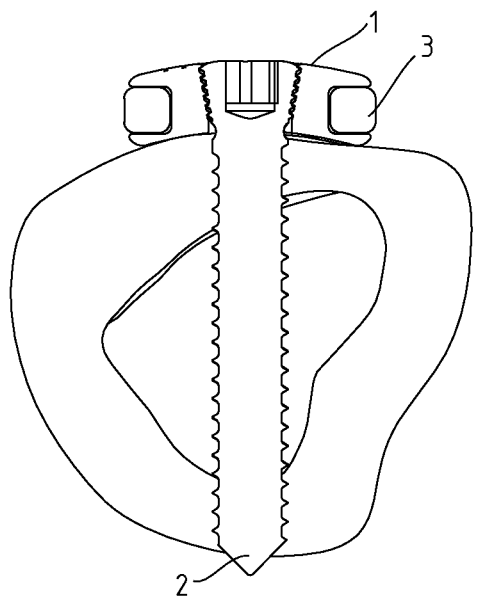
FIGS. 17a and 17b show in section two variants in which the rods have square, respectively round cross-section.
Figure 17B:
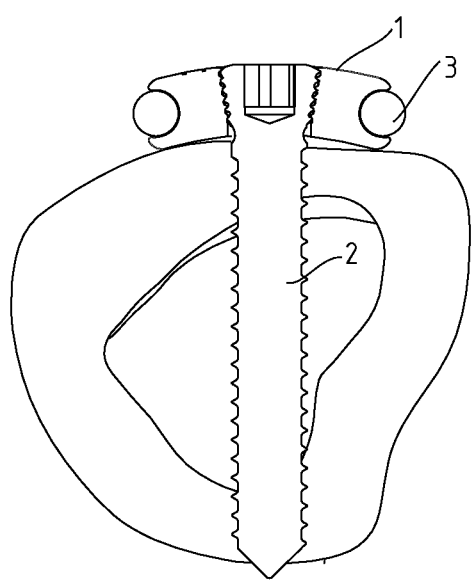

FIG. 16 illustrate another possible variant of the invention in which the connection rods 3 do not run in channels in the lower side of the plate, but on lateral channels. Importantly, in this variant, the rods do not touch the bone cortex, but are somewhat raised. In this arrangement the fracture zone is not directly in contact with any external body, which could be advantageous. Furthermore this structure is slightly more bendable than the previous ones in which the rods 3 were pressed lengthwise on the bone. As FIGS. 17a-b show, the connection rod can be square, round, or exhibit whichever cross-section.

Figure 18:
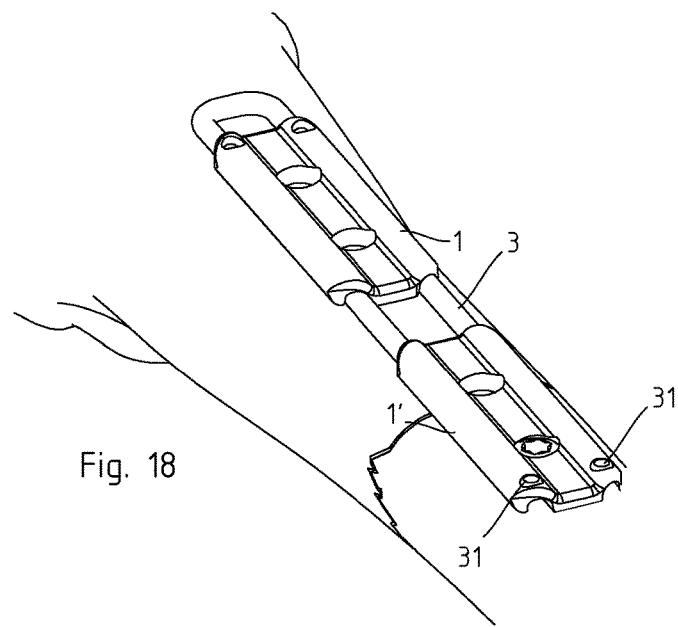
FIG. 18 illustrates, in the same anatomical location as the previous one, an embodiment of the present invention in which the plates have a central channel in their upper face, the screws being inserted in holes in the channel. Sinking the screws in the central channel, provides a reduction in height, thus an implant that is better suitable for small bones.
Figure 19A:
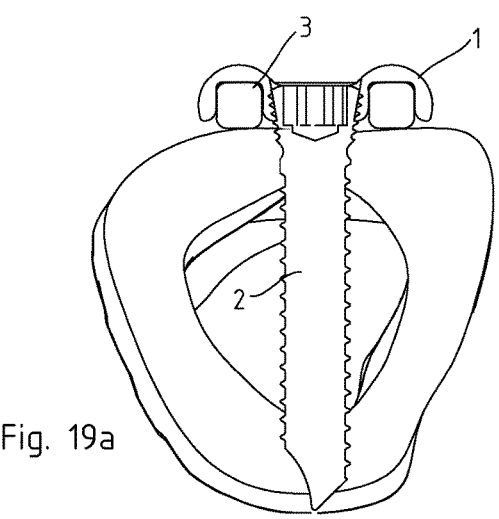
FIGS. 19a and 19b show two variant of this arrangement with square and round cross-section of the connection rods.
Figure 19B:
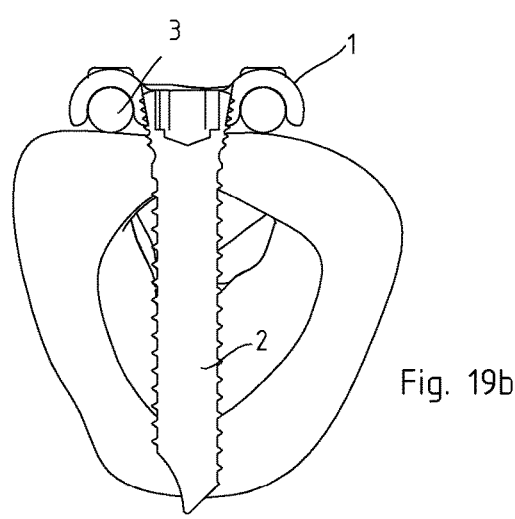

In some cases, limiting the height of the ostheosynthesis device may be desirable. This can be obtained for example by the embodiment shown in FIGS. 18, 19a-b, in which the plates 1, 1' have a channel on the upper face (the face opposed to that in contact with the bone) such that the screws 2 can be sunk deeper between the rails 3.

Figure 20:
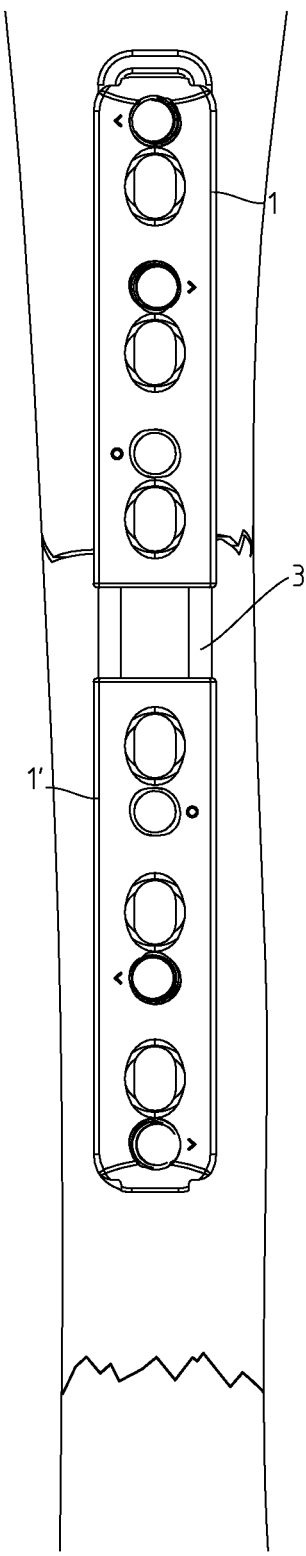
FIGS. 20 and 21 show a further embodiment of the present invention in which the connection rods run into longitudinal bores of the plates, such that they are integrally contained therein.
Figure 21:
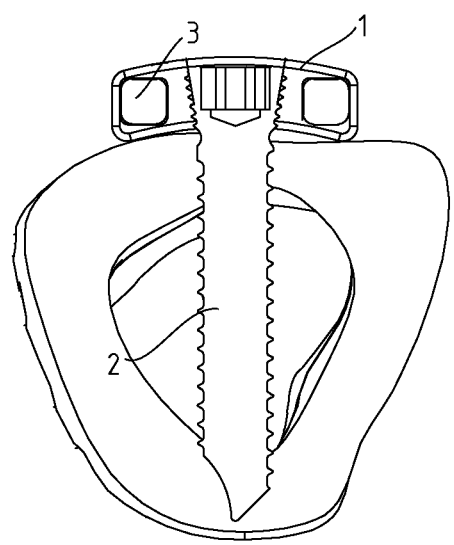

It is also possible to run the connection rods 3 inside longitudinal holes of the plates 1, 1'. In this case the rods are fully buried in the plates, as shown in the embodiment illustrated by FIGS. 20 and 21.

Another advantage of the device of the present invention lies in the fact that the bone fragments are not rigidly blocked, but on the contrary, the connection rods 3 present a certain amount of flexibility, that allows minute movements of the bone fragments, as already mentioned. The measure of flexibility can be adapted by choosing the thickness and length of the connection rods, and the number and the position of the fixation screws 2.

Another important advantage of the ostheosynthesis device of the invention is that its components can be inserted individually in the body and assembled on the implant site. Thanks to this, less invasive surgical techniques are possible.

The number of plates that are on the connection rods is not limited to two either, and the present invention includes as well variants in which three or more plates are connected by one pair of parallel rods. Notably, multi-plate combination can be used in the treatment of complicated and multiple fractures.

Importantly, the flexibility of the device can be modified also after the implant, by loosening or removing some or all of the screws, if the initial configuration proves to be too rigid or too flexible.

The present description is limited, for concision's sake, to a specific fixation device. The invention, however does encompass any plate, osteosynthesis device, reconstruction plate, or intramedullary implant, or acting as an osteoinductor to arthoplasty fixation and to the Artrodesis bones coming within the scope of the appended claims and their equivalents.

The invention claimed is:

1. Implantable bone fixation apparatus comprising a pair of plates provided with holes for receiving compression and/or locking screws that fasten the fixation system to the bone and with longitudinal slots, wherein a union element is disposed between the plates such as to bridge the bone parts that need to be united, the union element comprising one rod or several rods that cooperate with the longitudinal slots of the plates, wherein the longitudinal slots are on a lower side of the plates, and wherein both plates are provided with embedded transducer transmitting a local value of an electric or magnetic field at the fracture region, so as to allow stimulating the healing process and measuring and monitoring the mechanical stress at the fracture site, said transducer being connected to an external RFD interface so as to provide a feedback loop adapted to both controlling precisely the field at the bone level and monitor the healing process.

2. Implantable bone fixation according to claim 1, including embedded electronic, magnetic or microfluidic devices.

3. Implantable bone fixation according to claim 2, the embedded electronic, magnetic or microfluidic devices are included in screws lodged in at least some holes or are affixed to the plates.

4. Implantable bone fixation according to claim 2, said devices including permanent magnets or electromagnets generating a magnetic field between 0.1 and 4000 gauss.

5. Implantable bone fixation according to claim 2, said devices including a generator of a time-variable electric or magnetic field or a vibration source.

6. Implantable bone fixation according to claim 2, said devices including a magnetic transducer, or a strain gauge, or a position transducer, or a force transducer.

7. Implantable bone fixation according to claim 2, said devices including an energy source.

8. Implantable bone fixation according to claim 1, characterized by having one plate with slot disposed in an "H" configuration forming a wall hindering the movement of the plate in both directions.

9. Implantable bone fixation according to claim 1, wherein the plates have a central recess on the upper side.

10. Implantable bone fixation according to claim 1, wherein the plates have curved surfaces.

11. Implantable bone fixation according to claim 1, wherein the rods of the union element are tubular.

12. Implantable bone fixation according to claim 1, further comprising a strain, force or displacement transducer determining the mechanical stress at a fracture site to monitor the healing process.

13. Implantable bone fixation according to claim 12, said transducer including a strain gauge or MEMS sensors.

14. Implantable bone fixation according to claim 1, wherein the embedded electronic or magnetic devices generate a vibration stimulation.

* * * * *